Jan. 23, 1962 J. H. THOMPSON, JR Plant Pat. 2,123
ROSE PLANT
Filed March 6, 1961
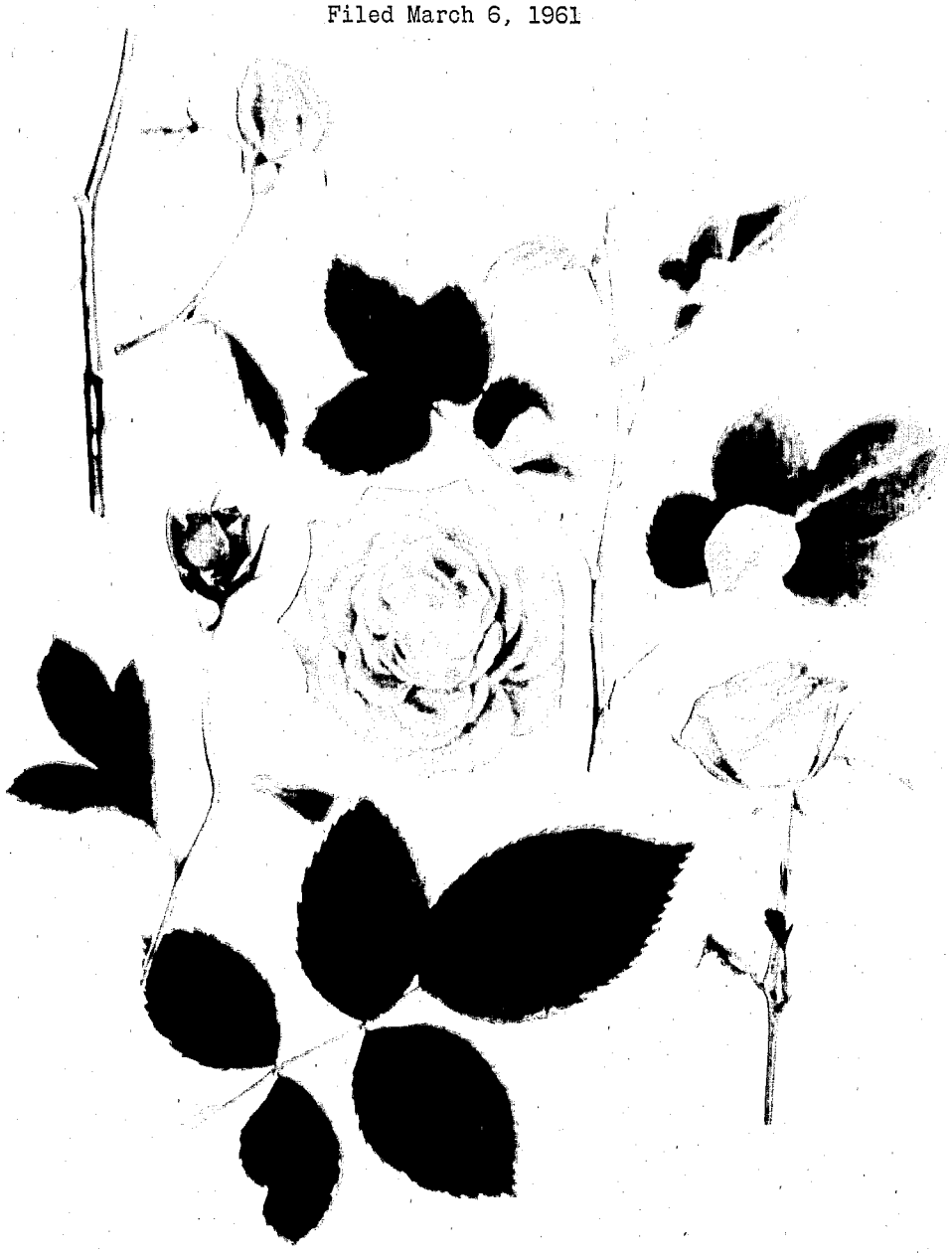
Inventor.
J. H. Thompson, Jr
By: Robb & Robb
Attorneys.

United States Patent Office

Plant Pat. 2,123
Patented Jan. 23, 1962

2,123
ROSE PLANT

Joshua Howard Thompson, Jr., Kennett Square, Pa., assignor to J. H. Thompson's Sons, Kennett Square, Pa., a partnership Filed Mar. 6, 1961, Ser. No. 93,822
1 Claim. (Cl. 47—61)

The present invention relates to a new and distinct variety of rose plant of the hybrid polyantha class, which originated as a sport of the variety "Garnette" (unpatented).

This new sport was discovered by me amongst a bed of "Garnette" plants which were being grown in greenhouses located on the property of my assignee, of which I am a partner, at Kennett Square, Pennsylvania, said "Garnette" plants then being grown under my supervision and control for cut flower purposes.

During the cultivation of these "Garnette" plants aforesaid, my attention was attracted to one particular branch of a plant that appeared to be bearing flowers distinctly different from those on the other parts of this particular plant which were typical of the variety "Garnette." Upon close examination of this particular plant, I found that it had sported, and I thereupon took steps to carefully preserve the sport, keep it under observation and to later asexually reproduce the same. These observations and asexual reproductions as performed by both budding and own-root cuttings at Kennett Square, Pennsylvania, conclusively established important differences between the sport and the parent variety "Garnette," and that these differing characteristics were fixed and established, and capable of being transmitted through succeeding propagations.

I am convinced that this new sport represents a new and distinct variety which is distinguished from its parent, as well as from all other varieties, as evidenced by the following unique combination of characteristics with which the sport is endowed:

(1) A vigorous growing habit;

(2) A distinctive luminescent Dark Rose Red general color tonality of the flowers; and (3) A greater depth of color that is apparent on both surfaces of the flower petals, thereby giving the flowers a dark red general coloration quite different from the dark pink general coloration that is typical of the flowers of the parent variety "Garnette."

Other than the aforementioned color differences and more vigorous habit of growth of my new variety, it conforms to its parent variety "Garnette" in habit of growth, foliage, flower form and petalage.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious:

Type: Hardy; greenhouse; sport; for cut flowers.
Class: Hybrid polyantha.
Parentage: Sport of "Garnette."
Propagation: Holds its distinguishing characteristics through succeeding propagations by cuttings, grafting and budding.

*Flowers*

Locality where grown and observed: Kennett Square, Pennsylvania.
Flowers borne: Singly; on strong and short stems.

Quantity of bloom: Abundant in greenhouse.
Continuity: Continuous.
Fragrance: Slight.
Bud:
*Peduncle.*—Short; medium caliper; stiff; smooth; with green prickles. Color—green.
*Before calyx breaks.*—Size—small. Form—medium length; without foliaceous appendages on the surface of the bud; with bristle-like foliaceous parts extending beyond the tip of the bud equal to ¼ of its length.
*As calyx breaks.*—Color—Garnet Lake, Plate 828.
*As first petal opens.*—Form—medium length. Color: outside—near Tyrian Purple, Plate 727, shaded with Garnet Lake, Plate 828, with point of attachment near white and separated from the main body color by a narrow band of Tyrian Purple, Plate 727; inside—a luminescent Rose Red slightly darker than Plate 724, with point of attachment Pod Green, Plate 061/1.
*Opening.*—Opens up well.
Bloom:
*Size (when fully open).*—Small; from 1½ to 2 inches.
*Petalage.*—Very double; from 45 to 55 petals; arranged regularly.
*Form.*—Cupped at first, but becoming flat; petals at first being tightly cupped and rolled outward, but later becoming tightly rolled outward at maturity.
Petals:
*Texture.*—Medium thickness; with both inside and outside velvety.
*Shape.*—Outer petals—round, with 2 notches. Intermediate petals—ovate, with 1 notch. Inner petals—ovate.

This description of a newly opened flower was made from a rose grown in a greenhouse during the month of November at Kennett Square, Pennsylvania:

*Color.*—Outer petal: outside surface—near Chrysanthemum Crimson, Plate 824/2, grading to Chrysanthemum Crimson, Plate 824/1 towards base of petal, with point of attachment Pod Green, Plate 061/1; inside surface—a luminescent Rose Red, somewhat darker than Plate 724, often with a streak of Pod Green, Plate 061/3 radiating from the base of the petal, and with point of attachment Pod Green, Plate 061/2, bordered by small areas of near white tinged with Mallow Purple, Plate 630/2 on either side of midrib. Intermediate petal: outside surface—near Chrysanthemum Crimson, Plate 824/2, with point of attachment Pod Green, Plate 061/1; inside surface—a luminescent Rose Red somewhat darker than Plate 724, with point of attachment Pod Green, Plate 061/1. Inner petal: outside surface—between Chrysanthemum Crimson, Plate 824/2 and Chrysanthemum Crimson, Plate 824/1, with point of attachment Pod Green, Plate 061/3; inside surface—a luminescent Rose Red somewhat darker than Plate 724, with point of attachment Pod Green, Plate 061/3.

This description was made from a rose that was open for three days in a greenhouse during the month of November at Kennett Square, Pennsylvania:

*Color.*—Outer petal: outside surface—near Tyrian Purple, Plate 727/1, with point of attachment Pod Green, Plate 061/3; inside surface—a luminescent Rose Red slightly larger than Plate 724, and often with streaks or irregular markings of near white on the lower half of the petal. Inner petal: outside surface—Chrysanthemum Crimson, Plate 824/3, with base of petal near white; inside surface—between Rose Red, Plate 724 and Chrysanthemum Crimson, Plate 824, becoming near white at base of petal, and with point of attachment Pod Green, Plate 061/2.

*General color effect.*—Newly opened flower—a luminescent Rose Red of a slightly darger shade than Plate 724. 3 days open—a luminescent Rose Red of a slightly darger shade than Plate 724.

*Behavior.*—Persist.

*Flower longevity.*—Cut roses grown in greenhouse and kept at living room temperatures—from 7 to 10 days in August.

*Reproductive organs*

Stamens: Medium number; arranged irregularly about pistils; mixed with petaloids.

Filaments: With short anthers. Color—Pod Green, Plate 061.

Anthers: Seldom anther fused with a petaloid. Color—Chrome Yellow, Plate 605.

Pollen: Moderate abundance. Color—gold.

Pistils: Medium number.

Styles: Uneven; medium length; thin; bunched.

Stigma: Color—yellow.

Ovaries: All enclosed in receptacle.

Hips: None observed.

Sepals: Permanent; medium length; spear-shaped.

Seeds: None observed.

*Plant*

Foliage:

*Leaves.*—Compound of 5–7 leaflets; abundant; medium size; moderately leathery.

*Leaflets.* — Shape — ovoid, with apex acuminate. Base—obtuse. Margin—simply serrate.

*Color.*—Mature: upper surface—Parsley Green, Plate 00962; under surface—between Sage Green, Plate 000861/1 and Sage Green, Plate 000861/2. Young: upper surface—near Spinach Green, Plate 0960, heavily overlaid with Oxblood Red, Plate 00823; under surface — Willow Green, Plate 00862/2, lightly overlaid with near Oxblood Red, Plate 00823/3.

*Rachis (the supporting stem of compound leaf).*—Medium caliper. Upper side—grooved. Under side—sparsely thorny.

*Stipules.*—Short; medium width; with points of medium length turning out at an angle of about 45°.

*Disease resistance.*—Comparable to the average variety grown under the same cultural conditions at Kennett Square, Pennsylvania.

Growth:

*Habit.*—Bushy; upright; much-branched.

*Growth.*—Vigorous.

*Canes.*—Medium caliper.

*Main stems.*—Color—Spinach Green, Plate 0960/2. Prickles—Color—Fern Green, Plate 0862/1. Hairs—Color—Spinach Green, Plate 0960/2.

*Branches.*—Color—Spinach Green, Plate 0960/2. Prickles — Color — Fern Green, Plate 0862/2. Hairs—color—Spinach Green, Plate 0960/2.

*New shoots.*—Color—Lettuce Green, Plate 861. Prickles — color — near Oxblood Red, Plate 00823/3. Hairs—few; color—near Oxblood Red, Plate 00823/3.

I claim:

A new and distinct variety of rose plant of the hybrid polyantha class, substantially as herein shown and described, characterized particularly as to novelty by the unique combination of general similarities to its parent variety "Garnette" (unpatented), but being essentially distinguished therefrom by a more vigorous habit of growth, a distinctive luminescent Dark Rose Red general color tonality of the flowers, and a greater depth of color on both surfaces of the flower petals which gives the flowers a darker red general coloration as compared with the dark pink general coloration of the flowers of "Garnette."

No references cited.